United States Patent
Nakamichi et al.

(10) Patent No.: US 6,312,726 B1
(45) Date of Patent: Nov. 6, 2001

(54) GASTRIC REMAINING PREPARATION, SWOLLEN MOLDING, AND PRODUCTION PROCESS

(75) Inventors: Kouichi Nakamichi, Shiga; Shougo Izumi, Kyoto; Hiroyuki Yasuura, Shiga, all of (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 0 days.

(21) Appl. No.: 08/591,682

(22) PCT Filed: Aug. 18, 1994

(86) PCT No.: PCT/JP94/01367

§ 371 Date: Feb. 20, 1996

§ 102(e) Date: Feb. 20, 1996

(87) PCT Pub. No.: WO95/05809

PCT Pub. Date: Mar. 2, 1995

(30) Foreign Application Priority Data

Aug. 20, 1993 (JP) .................................... 5-227878

(51) Int. Cl.$^7$ ............................ A61K 47/32; A61K 47/38
(52) U.S. Cl. ............................................ 424/487; 424/488
(58) Field of Search ..................................... 424/484, 487, 424/488

(56) References Cited

U.S. PATENT DOCUMENTS

| | | | |
|---|---|---|---|
| 4,493,807 | * 1/1985 | Vyvial et al. | 264/101 |
| 4,738,817 | * 4/1988 | Wittwer et al. | 264/328.14 |
| 4,880,585 | * 11/1989 | Klimesch et al. | 264/141 |
| 5,073,379 | * 12/1991 | Klimesch et al. | 424/467 |

FOREIGN PATENT DOCUMENTS 0 326 816 A   8/1989 (EP).

* cited by examiner

*Primary Examiner*—Peter F. Kulkosky
(74) *Attorney, Agent, or Firm*—Graham & James LLP

(57) ABSTRACT

A gastric remaining preparation having a configuration entirely different from that of the conventional ones. It comprises a swollen molding having a mesh-like cross-section and an apparent density of less than 1, containing an acid-resistant polymer compound as a predominant component as well as at least an auxiliary blowing agent and a drug substance. The molding can be produced by using a multi-screw extruder.

8 Claims, 3 Drawing Sheets

GASTRIC REMAINING PREPARATION, SWOLLEN MOLDING, AND PRODUCTION PROCESS

This application is a 371 of PCT/JP94/01367 filed August.

TECHNICAL FIELD

The present invention relates to a gastric remaining preparation. More particularly, the present invention relates to a swollen molding that can be manufactured by means of a multi-screw extruder and a gastric remaining preparation comprising the same.

A gastric remaining preparation is a pharmaceutical device adapted to remain afloat on top of the gastric juice and contents and release an active drug substance in situ in a retarded fashion.

The term "swollen molding" is used herein to mean an artifact containing internal pores as swollen and formed under the influence of heat and/or pressure or through other phenomena such as chemical change.

BACKGROUND ART

Being a kind of controlled-release preparation, the gastric remaining preparation offers the advantages of a reduced frequency of administration, sustained effective concentration, and mitigated side effects. In addition, the gastric remaining preparation is more or less indifferent to the gastric emptying rate so that the drug substance may be released in sufficient quantities at the absorption site. Therefore, any gastric remaining preparation is a very useful medical device and this is particularly true for those drug substances which are expected to act directly on the stomach or the upper part of the small intestine.

Among the hitherto-known gastric remaining preparations are the preparation exploiting a hydrophilic colloid (JP-A-58057315), the preparation comprising a hollow molded structure externally coated with an active substance (JP-A-55012411), the one utilizing foamable microcapsules (JP-A-52076418), the one comprising a mixture of a water-soluble polymer and an oil and fat with the specific gravity of the whole mixture having been controlled to not greater than 1 (JP-A-61043108, PCT WO91/06281), and the one comprising foamed ethylcellulose (JP-A-62145014), among others. While some of them are functionally acceptable gastric remaining preparations, many are intricate in structure and destroyed by the peristolic motion of the stomach to lose the expected floatability.

Meanwhile, the multi-screw extruder is a kind of screw kneading extruder which is quite different from the single-screw extruder in performance mode and application. Unlike the single-screw extruder which is a simple kneading extruder, the multi-screw extruder has a mechanism resembling an Archimedian screw pump which delivers a high energy output physically through the intermeshing and mutual interference of a plurality of screws, with the result that the load can be subjected to treatments not provided by the single-screw extruder. The multi-screw extruder has been elaborated chiefly in the food and plastics industries and is in common usage for the processing of food (cereals, protein, animal meat, fish meat, etc.) and the injection molding of plastics.

Technologies utilizing an extruder in the pharmaceutical field are disclosed in PCT WO92/18106, PCT WO093/01472, and JP-A-5194197, among other literature. These technologies are not concerned with intragastric resident preparations but are directed to pharmaceutical preparations differing from gastric remaining preparations in construction and effect.

Known in the field of food are several technologies by which swollen moldings are manufactured from certain food materials (e.g. starch materials) using a multi-screw extruder (JP-A-5284926, JP-A-5192083, JP-A-5023125, JP-A-4051849, JP-A-1252267, JP-A-61009253, etc.). However, these technologies are invariably designed to solve the problems characteristic of food industry (promotion of appetite, improvement of appearance, etc.) and belong to a different technical field.

Also known is a technology wherein a swollen molding called an interpenetrating polymer network structure composed predominantly of a lactic acid type polymer (e.g. polylactic acid) is provided by means of a screw extruder (JP-A-5177734). However, this swollen molding is designed for use as an absorbent or filter material for oil and body fluids. Moreover, swollen moldings of this type have a high affinity for water so that they are not adaptable to gastric remaining preparation.

DISCLOSURE OF INVENTION

The primary object of the present invention is to provide a gastric remaining preparation which is quite different in structure from any conventional gastric remaining preparation.

The inventors of the present invention who had been assiduously exploring the utility of a multi-screw extruder (hereinafter referred to briefly as an extruder) in the pharmaceutical field arrived at a gastric remaining preparation meeting the above object and completed the present invention.

The gastric remaining preparation of the present invention (hereinafter referred to briefly as the preparation of the invention) comprises a swollen molding of the present invention (hereinafter referred to as the swollen molding of the invention). The preferred preparation of the invention is a preparation having an apparent density of less than 1.

The swollen molding of the invention is an expanded structure having a mesh-like cross-section and an apparent density of less than 1, which structure being predominantly composed of an acid-resistant polymer compound and additionaly containing at least an auxiliary blowing agent and a drug substance. Because of its being mesh-like in cross-section, the swollen molding of the invention has a multiplicity of microfine internal pores which are continuous or discontinuous.

Credit is due to the inventors of the present invention for the first creation of a gastric remaining preparation by means of an extruder.

Figure 1:
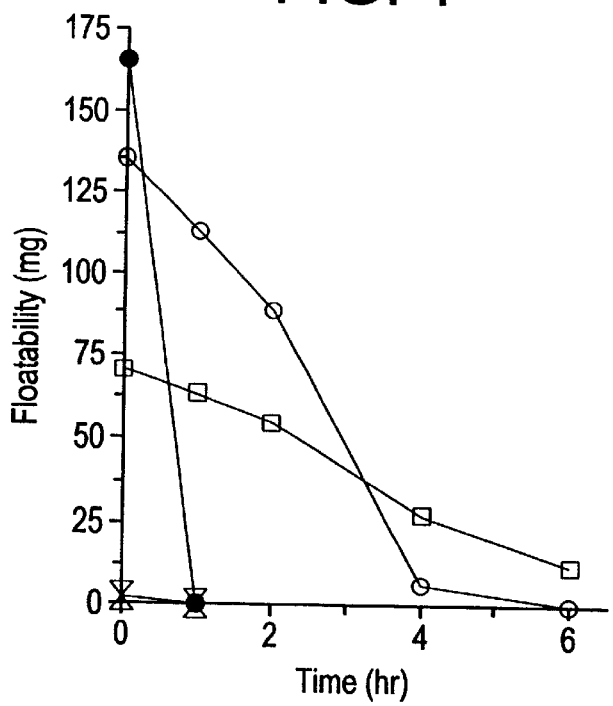
FIG. 1 is a graph of floatability characteristics.

In the first place, the swollen molding of the invention is now described in detail.

The swollen molding of the invention is predominantly composed of an acid-resistant polymer compound and, as such, is substantially insoluble in neutral through acidic aqueous media, thus being resistant to gastric acidity. The term "predominantly composed" as used herein means that, of all the components of the artifact, the particular component accounts for the largest proportion.

The acid-resistant polymer compound that can be used includes the pH-dependent or pH-independent coating agent which is conventionally used in the manufacture of pharmaceutical products. Typically, there can be mentioned hydroxypropylmethylcellulose acetate succinate (Aqoat-L, M, H; registered trademark), hydroxypropylmethylcellulose phthalate (HP-50, 55, 55S), methacrylate copolymer L, S (Eudragit-L30D55, L100, L100-55, S100; registered trademark), carboxymethylethylcellulose (CMEC; registered trademark), cellulose acetate phthalate (CAP; registered trademark), ethylcellulose, and aminoalkyl methacrylate copolymer RS (Eudragit-RS, RN100L, RN100, RSPML, RSPM; registered trademark), among others.

The acid-resistant polymer compounds mentioned above can be used singly or in combination. Thus, even when two or more species are used, the object of the invention can be sufficiently accomplished.

The proportion of the acid-resistant polymer compound is dependent on the selected species of auxiliary blowing agent and drug substance, and the desired swollen molding or gastric remaining preparation of the invention but may range suitably from 25 to 94% (w/w), preferably 40–80% (w/w), and for still better results, 50–70% (w/w). With a proportion of less than 25% (w/w), the desired acid resistance and strength of the product may not be fully obtained.

The auxiliary blowing agent is an additive used for generating a multiplicity of microfine pores or air spaces uniformly distributed within the swollen molding.

This auxiliary blowing agent is considered to exert a pseudozeolitic action on the load in the process of production of a swollen molding using an extruder which is described hereinafter. In the absence of such an auxiliary blowing agent, the swollen molding of the invention can hardly be obtained using an extruder. Therefore, the auxiliary blowing agent is a component of great importance to the present invention.

The auxiliary blowing agent that can be used includes dried aluminum hydroxide gel, synthetic aluminosilicate, calcium hydrogen phosphate, calcium carbonate, precipitated calcium carbonate, sodium hydrogen carbonate, calcium hydrogen carbonate, and talc, to name but a few.

The above-mentioned auxiliary blowing agent may be used singly or in combination. Even when two or more species are employed, the object of the invention can be sufficiently accomplished.

The proportion of the auxiliary blowing agent depends on the selected species of polymer compound, auxiliary blowing agent and drug substance, and the desired swollen molding or gastric remaining preparation of the invention but may range suitably from 5 to 40% (w/w), preferably 10–30% (w/w), and for still better results, 15–20% (w/w). With a proportion of less than 5% (w/w), sufficiently uniform, microfine pores may not be obtained. With a proportion in excess of 40% (w/w), the apparent morphology characteristic of the swollen molding of the invention can be obtained depending on cases but the molding may be inadequate in acid resistance and strength of the product.

The drug substance that can be used in accordance with the present invention is not particularly limited but is preferably a substance stable against heat. The following is a partial list of specific drug substances that can be used.

1. Antipyretic, Analgesic and Antiinflammatory Agents

Indomethacin, aspirin, diclofenac sodium, ketoprofen, ibuprofen, mefenamic acid, dexamethasone, dexamethasone sodium sulfate, hydrocortisone, prednisolone, azulene, phenacetin, isopropylantipyrine, acetaminophen, benzydamine hydrochloride, phenylbutazone, flufenamic acid, sodium salicylate, choline salicylate, Sasapyrine (salsalate), clofezone, etodolac.

2. Antiulcer agents

Sulpiride, cetraxate hydrochloride, gefarnate, irsogladine maleate, cimetidine, ranitidine hydrochloride, famotidine, nizatidine, roxatidine acetate hydrochloride.

3. Coronary vasodilators

Nifedipine, diltiazem hydrochloride, trapidil, dipyridamole, dilazep dihydrochloride, methyl 2,6-dimethyl-4-(2-nitrophenyl)-5-(2-oxo -1,3,2-dioxaphosphorinan-2-yl)-1,4-dihydropyridine-3-carboxylate, verapamil, nicardipine, nicardipine hydrochloride, verapamil hydrochloride.

4. Peripheral vasodilators

Ifenprodil tartrate, cinepazide maleate, cyclandelate, cinnarizine, pentoxiphylline.

5. Antibiotics

Ampicillin, amoxicillin, cefalexin, erythromycin ethyl succinate, bacampicillin hydrochloride, minocycline hydrochloride, chloramphenicol, tetracycline, erythromycin.

6. Synthetic antimicrobial agents

Nalidixic acid, piromidic acid, pipemidic acid trihydrate, enoxacin, cinoxacin, ofloxacin, norfloxacin, ciprofloxacin hydrochloride, sulfamethoxazole-trimethoprim, 6-fluoro-1-methyl-7-[4-(5-methyl-2-oxo-1,3-dioxolen-4-yl)methyl-1-piperazinyl]-4-oxo-4H[1,3]thiazeto[3,2-a]quinoline-3-carboxylic acid.

7. Propantheline bromide, atropine sulfate, oxapium bromide, timepidium bromide, scopolamine butylbromide, trospium chloride, butropium bromide, N-methylscopolamine methylsulfate, octatropine methylbromide.

8. Antitussive and antiasthmatic agents

Theophylline, aminophylline, methylephedrine hydrochloride, procaterol hydrochloride, trimethoquiinol hydrochloride, codeine phosphate, cromoglicate sodium, tranilast, dextromethorphan hydrobromide, dimemorfan phosphate, clobutinol hydrochloride, fominoben hydrochloride, benproperine phosphate, tipepidine hibenzate, eprazinone hydrochloride, clofedanol hydrochloride, ephedrine hydrochloride, noscapine, carbetapentane citrate, oxeladin tannate, isoaminile citrate.

9. Bronchodilators

Diprophylline, salbutamol sulfate, clorprenaline hydrochloride, formoterol fumarate, orciprenaline sulfate, pirbuterol hydrochloride, hexoprenaline sulfate, bitolterol mesilate, clenbuterol hydrochloride, terbutaline sulfate, mabuterol hydrochloride, fenoterol hydrobromide, methoxyphenamine hydrochloride.

10. Diuretic agents

Furosemide, acetazolamide, trichlormethiazide, methyclothiazide, hydrochlorothiazide, hydroflumethiazide, ethiazide, cyclopentiazide, spironolactone, triamterene, florothiazide, piretanide, mefruside, etacrynic acid, azosemide, clofenamide.

11. Muscle relaxants

Chlorophenesin carbamate, tolperisone hydrochloride, eperisone hydrochloride, tizanidine hydrochloride, mephenesin, chlorzoxazone, phenprobamate, methocarbamol, chlormezanone, pridinol mesilate, afloqualone, baclofen, dantrolene sodium.

12. Nootropic agents

Meclofenoxate hydrochloride.

13. Minor tranquilizers

Oxazolam, diazepam, clotiazepam, medazepam, temazepam, fludiazepam, meprobamate, nitrazepam, chlordiazepoxide.

14. Major tranquilizers

Sulpiride, clocapramine hydrochloride, zotepine, chloropromazine, haloperidol.

15. β-Blockers

Pindolol, propranolol hydrochloride, carteolol hydrochloride, metoprolol tartrate, labetalol hydrochloride, acebutolol hydrochloride, bufetolol hydrochloride, alprenolol hydrochloride, arotinolol hydrochloride, oxprenolol hydrochloride, nadolol, bucumolol hydrochloride, indenolol hydrochloride, timolol maleate, befunolol hydrochloride, bupranolol hydrochloride.

16. Antiarrhythmic agents

Procainamide hydrochloride, disopyramide, ajmaline, quinidine sulfate, aprindine hydrochloride, propafenone hydrochloride, mexiletine hydrochloride.

17. Antigout agents

Allopurinol, probenecid, colchicine, sulfinpyrazone, benzbromarone, bucolome.

18. Anticoagulants

Ticlopidine hydrochloride, dicoumarol, warfarin potassium.

19. Antiepileptics

Phenytoin, sodium valproate, metharbital, carbamazepine.

20. Antihistaminics

Chlorpheniramine maleate, clemastine fumarate, mequitazine, alimemazine tartrate, cyproheptadine hydrochloride.

21. Antiemetics

Difenidol hydrochloride, metoclopramide, domperidone, betahistine mesilate, trimebutine maleate.

22. Antihypertensive agents

Dimethylaminoethyl reserpilinate hydrochloride, rescinnamine, methyldopa, prazosin hydrochloride, bunazosin hydrochloride, clonidine hydrochloride, budralazine, urapidil.

23. Sympathomimetic agents

Dihydroergotamine mesilate, isoproterenol hydrochloride, etilefrine hydrochloride.

24. Expectorants

Bromhexine hydrochloride, carbocysteine, cysteine ethyl ester hydrochloride, cysteine methyl ester hydrochloride.

25. Oral antidiabetic agents

Glibenclamide, tolbutamide, glymidine sodium.

26. Cardiovascular system drugs

Ubidecarenone, ATP-2Na.

27. Iron preparations

Ferrous sulfate, dried iron sulfate.

28. Vitamins

Vitamin $B_1$, vitamin $B_2$, vitamin $B_6$, vitamin $B_{12}$, vitamin C, folic acid.

29. Therapeutic agents for pollakiuria

Flavoxate hydrochloride, oxybutynin hydrochloride, terodiline hydrochloride, 4-diethylamino-1,1-dimethyl-2-butynyl (±)-α-cyclohexyl-α-phenylglycolate hydrochloride monohydrate.

30. Angiotensin converting enzyme inhibitors Enalapril maleate, alacepril, delapril hydrochloride.

The proportion of the drug substance depends on the selected species of acid-resistant polymer compound, auxiliary blowing agent and drug substance, and the desired swollen molding or gastric remaining preparation of the invention but may range suitably from 0.01–45% (w/w), preferably 1–20% (w/w), and for still better results, 5–15% (w/w). Depending on the type of drug substance, the morphology characteristic of the swollen molding of the invention may be obtained even with less than 0.01% (w/w) of the drug substance but sufficient acid resistance and strength of the product may not be obtained when the proportion of the drug substance exceeds 45% (w/w).

In addition, a drug release control agent, a plasticizer, a fluidizing agent, etc. may also be incorporated as necessary.

The drug release control agent may be a substance which dissolves or swells upon contact with acid or water and as such includes hydroxypropylcellulose, hydroxypropylmethylcellulose, methylcellulose, polyvinyl acetal diethylaminoacetate, polyvinylpyrrolidone, polyvinyl alcohol, wheat flour, corn starch, mannitol, lactose, microcrystalline cellulose, low substituted hydroxypropylcellulose, and so on.

Such drug release control agents can be used singly or in combination. Even when two or more species are used, the object of the present invention is sufficiently accomplished.

The drug release control agent can be incorporated up to about 45% (w/w) of the whole composition. With a proportion exceeding 45% (w/w), the acid resistance and strength of the product may not be sufficient. The term "drug release control agent" means a substance that controls the rate of release of a drug substance from a preparation.

The plasticizer and fluidizing agent are not limited in kind but can be those conventionally employed in the manufacture of pharmaceutical products. Thus, polyethylene glycol, propylene glycol, glycerol, higher fatty acids (lauric acid, tridecanoic acid, myristic acid, pentadecanoic acid, palmitic acid, margaric acid, stearic acid, nonadecanoic acid, arachic acid, behenic acid, lignoceric acid, cerotic acid, montanic acid, etc.), higher fatty acid ester derivatives (e.g. the esters of the above-mentioned fatty acids with glycerol, ethylene glycol, propylene glycol, sorbitol, polyethylene glycol, etc.; saturated fatty acid glycerides of the animal or vegetable origin and mixtures thereof; hydrogenated oils available from glycerides of the animal or vegetable origin; and glycerides of unsaturated fatty acids such as oleic acid, linolic acid, linolenic acid, ricinoleic acid, etc. and mixtures thereof), higher alcohols (pentadecanol, hexadecanol, cetyl alcohol, heptadecanol, stearyl alcohol, nonadecanol, eicosanol, wool alcohol, cholesterol, etc.), and higher alcohol ester derivatives (cholesteryl palmitate, plant sterol palmitate, etc.) can be mentioned by way of example.

The above-mentioned plasticizer and fluidizing agent can be used singly or in combination. Even when two or more species are used, the object of the present invention can be sufficiently accomplished.

The plasticizer and fluidizing agent can be incorporated up to an upper limit of about 10% (w/w) of the whole composition. With a proportion in excess of 10% (w/w), poor expansion may be the outcome.

The plasticizer and fluidizing agent reduce the frictional resistance generated in the barrel structure to insure a smooth extruder processing.

The method for producing the swollen molding of the invention is now described in detail.

The swollen molding of the invention can be manufactured by using said acid-resistant polymer compound, auxiliary blowing agent, and drug substance as well as water as essential materials and processing them in a lump with an extruder.

The term "in a lump" as used herein means that all the components and water are subjected substantially concurrently to extruder actions such as shearing, blending, kneading, compression, and extrusion.

The extruder in general consists essentially of a series of hollow cylinders known as barrels, a die constituting an exit, and a screw means. The barrel structure usually comprises a plurality of barrels and the screw means extend therethrough. The screw is available in a variety of types such as trapezoidal screw, trapezoidal cut screw, trapezoidal reverse cut screw, ball screw and kneading paddle and they can be used in any desired combination. The load fed to the extruder is driven by the screw to travel down the barrel means, subjected to shearing and blending forces by the screw means, and extruded from the die orifice or orifices. Usually the temperatures of the respective barrels and die can be independently controlled.

The present invention can be carried into practice by utilizing an extruder having the fundamental functions of transporting, blending, compressing, crushing and heating water-rich or oil-rich loads which is commonly used in the food and plastic fields. Thus, any extruder having two or more screws can be employed for the purposes of the present invention. In this connection, the swollen molding of the invention can be obtained without trouble by using a twin-screw extruder, that is to say an extruder equipped with a couple of screws.

The processing in a lump with the extruder need not necessarily take place throughout the whole barrel structure and die of the extruder. The swollen molding of the invention can be obtained only provided the processing in a lump takes place in a certain segmental barrel of the barrel structure and on the path downstreams thereof.

Typical modes of processing in a lump with the extruder are (1) the mode in which all the components (i.e. acid-resistant polymer compound, auxiliary blowing agent, drug substance, etc.) and water are pre-kneaded and fed through the main feeding port of the extruder for processing in a lump, (2) the mode in which all the components are pre-mixed and fed through the main feeding port of the extruder and water is fed through the auxiliary feeding port of the extruder for processing in a lump, (3) several of the components are premixed and fed through the main feeding port of the extruder and the remaining component or components and water are fed through the auxiliary feeding port of the extruder for processing in a lump, and (4) the mode in which one of the components is fed through the main feeding port of the extruder and the remaining components are fed through the auxiliary feeding port of the extruder for processing in a lump. Among the above-mentioned modes, mode (2) or (3) is preferred.

The term "main feeding port" is used herein to mean the most basic feeding port through which the load can be fed into the barrel structure, while the term "auxiliary feeding port" is used herein to mean any supplemental feeding port other than the main feeding port that is available for feeding water and additives.

In the above mode (1), any of the components and/or water can be further introduced from such an auxiliary feeding port as necessary.

In the above mode (2), any of the components can be further introduced from said auxiliary feeding port.

In the mode (3), said several of the components may be the acid-resistant polymer compound and drug substance and said remaining components may be the auxiliary blowing agent and other components. Preferably, the acid-resistant polymer compound is included among said several of the components. The remaining components can be fed either as a mixture through one and same auxiliary feeding port or independently or as mixtures of more than one component each through a plurality of auxiliary feeding ports. In any case, the swollen moldi of the invention can be successfully obtained. It is also possible to transfer one or more of said several of the components to be introduced through the main feeding port to a feed consisting of said remaining components and feed it or them through the auxiliary feeding port.

In the above mode (4), said one component is preferably the acid-resistant polymer compound. The remaining components can be fed either as a mixture through one and same auxiliary feeding port or independently or as mixtures of more than one component each through a plurality of auxiliary feeding ports. In any event, the swollen molding of the invention can be obtained. It is also possible to transfer said one component to be introduced through the main feeding port to a feed consisting of said remaining components and feed it through the auxiliary feeding port.

The premixing or prekneading of various components with or without addition of water can be carried out either manually or mechanically using a kneader-mixer, V-mixer, double-cone mixer, box mixer, ribbon mixer, or the like.

The supply of various components and water into the barrel structure can be effected either manually or using a feeder with which the extruder is generally equipped. Virtually any device that is capable of feeding the load at a constant speed can be employed. As examples of such device, there can be mentioned a screw feeder, a table feeder, a belt-conveyerized quantitative feeder, and an electromagnetic feeder, among other devices.

The relative amounts of respective components that are to be fed to the extruder can be judiciously selected within the ranges mentioned hereinbefore.

The proportion of water is dependent on the specific components selected, the model and type of extruder, processing conditions, and the objective swollen molding of the invention but may range from 5 to 20% (w/w) based on the total composition. With a proportion of less than 5% (w/w), either poor expansion or overloading due to increased intra-barrel frictional resistance and consequent extrusion failure may take place. When the limit of 20% (w/w) is exceeded, poor expansion may result.

The term "water" is used herein to cover not only mere water but also physiological saline and other isotonic aqueous solutions, neutral, acid or basic buffer solutions, aqueous ammonia and the like.

The extruder processing conditions are now described.

The barrel and die temperature of the extruder can be set at an appropriate level according to the specific components selected, the model and type of extruder, and the objective swollen molding of the invention, among other factors. Specifically, the temperature can be set at 70–150° C., preferably 100–120° C. The swollen molding of the invention can still be obtained at a temperature setting over 150° C. but an unnecessarily high temperature may decompose the drug substance. At temperatures below 70° C., the swollen molding of the invention may not be obtained.

The rotational speed of the screws can be selected, within the allowable range of the extruder, according to the model and type of extruder, the components to be processed, and screw geometry, among other factors. The greater the overall length of the extruder barrel structure is, the higher is the rotational speed of the screws that can be selected. This is because the longer the barrel structure, the higher is the processing capacity of the extruder. To be specific, a screw speed of not less than 50 rpm, preferably between 50 and 300 rpm, is appropriate.

The delivery pressure may be 10–150 kg/cm$^2$ and is preferably 30–120 kg/cm$^2$.

The screw configuration and combination can be freely selected without particular restriction.

However, it is preferable to include at least one paddle capable of yielding high kneading and shearing forces, known as the kneading paddle.

The delivery or exit die can be changed according to the objective swollen molding or preparation of the invention. Typical is a delivery die with an orifice diameter of 0.5–5 mm.

It is conjectured that the expansion response of the extruder load occurs when the load under appropriate temperature and high pressure conditions within the barrel structure is suddenly brought back to atmospheric pressure on emergence from the die. Moreover, the water contained in the load is simultaneously vaporized and the resulting water vapor also plays a part in the expansion response of the load.

The preparation of the invention is now described in detail.

The whole composition processed in a lump in the extruder emerges continuously from the die orifice or orifices. The extrudate can be cut to length with a suitable cutter means such as a roller granulator, a cutter mill, a pin mill or the like. The cuttings can be put to use as they are to provide a granular or fine granular preparation of the present invention. Moreover, when the swollen molding of the invention as extruded from the die orifice is cut to length using, for example, a revolving cutter means (e.g. a rotary cutter, 2-blade type, rotational speed 0–1750 rpm) mounted at the tip of the die, a granular or fine granular preparation of the present invention is directly obtained without resort to special size selection.

When cuttings of the swollen molding of the invention in the granular or fine granular form are filled in capsule shells or other containers with or without addition of a different drug substance or premix or an excipient, an encapsulated preparation of the present invention is obtained. When they are compressed, a tablet of the present invention is obtained.

Furthermore, the swollen molding of the invention as extruded from the die or cuttings thereof, such as granules or fine granules, can be coated and, then, filled in capsule shells to provide a preparation of the invention. In this case, the swollen molding and preparation of the invention can be improved in mechanical strength and in the stability of the drug substance.

EFFECTS OF INVENTION

Because of its enhanced mechanical strength and floatability, the preparation of the invention stays longer within the stomach than does the conventional intragastric resident preparation. Moreover, the preparation of the invention provides both of stable floatability and drug stable delivery.

The swollen molding (preparation) of the invention can be expediently manufactured using an extruder on a high production scale and basically in a continuous sequence. Therefore, the method for producing an swollen molding (preparation) of the invention is of great value for commercial purposes.

BEST MODE OF PRACTICING THE INVENTION

The following Examples, Comparison Examples, and Test Examples are intended to illustrate the present invention in further detail.

EXAMPLE 1

Twenty (20) grams of nicardipine hydrochloride, 110 g of hydroxypropylmethylcellulose acetate succinate (tradename: Aqoat, AS-MF, Shin-Etsu Chemical Co., Ltd; the same applies hereinafter), 30 g of dried aluminum hydroxide gel, and 90 g of wheat flour were admixed and fed through the hopper to the main feeding port of a twin-screw extruder (KEXN-30S-20, Kurimoto Ltd.; the same applies hereinafter) equipped with a couple of screws each having a diameter of 32 mmϕ/, an effective L/D ratio of 20, and a screw pattern of 16P, 12P, 9.6P, 8P, 30 deg, 8t×3·30 deg (reverse), and a die having five 1 mmϕ-orifices at a rate of 30 g/min. The operating temperature was set to 100° C. for the respective barrels and die and with purified water being fed through the auxiliary feeding port at a rate of 2 ml/min., the load was processed and extruded at a screw speed of 80 rpm to provide an swollen molding of the invention.

EXAMPLE 2

Twenty (20) grams of nicardipine hydrochloride, 200 g of hydroxypropylmethylcellulose acetate succinate, 20 g of dried aluminum hydroxide gel, and 10 g of wheat flour were admixed and the mixture was processed and extruded under the same conditions as in Example 1 to provide an swollen molding of the invention.

EXAMPLE 3

Twenty (20) grams of nicardipine hydrochloride, 217.5 g of hydroxypropylmethylcellulose acetate succinate, 12.5 g of dried aluminum hydroxide gel were admixed and the mixture was processed and extruded under the same conditions as in Example 1 to provide an swollen molding of the invention.

EXAMPLE 4

Twenty (20) grams of nicardipine hydrochloride, 155 g of hydroxypropylmethylcellulose phthalate (tradename: HPMCP, HP-55F grade, Shin-Etsu Chemical Co., Ltd; the same applies hereinafter), 25 g of dried aluminum hydroxide gel, and 50 g of wheat flour were admixed and the mixture was processed and extruded under the same conditions as in Example 1 to provide an swollen molding of the invention.

EXAMPLE 5

Twenty (20) grams of nicardipine hydrochloride, 60 g of hydroxypropylmethylcellulose acetate succinate, 60 g of ethylcellulose (tradename: Ethocel, STD-45 type, Dow Chemical; the same applies hereinafter), 30 g of anhydrous calcium hydrogen phosphate, and 80 g of polyvinyl acetal diethylaminoacetate (tradename: AEA, Sankyo Company, Limited; the same applies hereinafter) were admixed and the mixture was processed under the same conditions as in Example 1 except that the temperature of the barrels and die was set at 140° C. to provide an swollen molding of the invention.

EXAMPLE 6

Twenty (20) grams of oxybutynin hydrochloride, 150 g of hydroxypropylmethylcellulose acetate succinate, 30 g of dried aluminum hydroxide gel, and 50 g of corn starch were admixed and the mixture was processed under the same conditions as in Example 1 to provide an swollen molding of the invention.

EXAMPLE 7

Twenty (20) grams of oxybutynin hydrochloride, 100 g of ethylcellulose, 50 g of synthetic aluminosilicate, and 80 g of wheat flour were admixed and the mixture was fed through the hopper to the main feeding port of a twin-screw extruder equipped with the same screws and die as described in Example 1 at a rate of 30 g/min. With the barrel and die temperature being set at 120° C. and purified water being fed through the auxiliary feeding port at a rate of 4 ml/min., the load was processed and extruded at a screw speed of 100 rpm to provide an swollen molding of the invention.

EXAMPLE 8

Twenty (20) grams of oxybutynin hydrochloride, 150 g of ethylcellulose, 50 g of calcium carbonate, and 30 g of corn starch were admixed and the mixture was fed through the hopper to the main feeding port of a twin-screw extruder equipped with the same screws and die as described in Example 1 at a rate of 30 g/min. With the barrel and die temperature being set to 100° C. and a 50% (w/w) aqueous solution of propylene glycol being fed through the auxiliary feeding port at a rate of 2 ml/min., the load was processed and extruded at a screw rotational speed of 100 rpm to provide an swollen molding of the invention.

EXAMPLE 9

Twenty (20) grams of 4-diethylamino-1,1-dimethyl-2-butinyl(±)-α-cyclohexyl-α-phenylglycolate hydrochloride monohydrate, 180 g of hydroxypropylmethylcellulose acetate succinate, and 50 g of dried aluminum hydroxide gel were admixed and the mixture was fed through the hopper to the main feeding port of a twin-screw extruder equipped with the same screws as described in Example 1 and a 0.5 mmφ×15-orifice die at a rate of 20 g/min. With the barrel and die temperature being set at 90° C. and a 50% (w/w) aqueous solution of propylene glycol being fed through the auxiliary feeding port at a rate of 2 ml/min., the load was processed and extruded at a screw rotational speed of 100 rpm to provide an swollen molding of the invention.

EXAMPLE 10

Twenty (20) grams of rivoflavine, 150 g of aminoalkyl methacrylate copolymer RS (tradename: Eudragit, RSPM; distributor: Higuchi Shokai), 30 g of talc, and 50 g of polyvinylpyrrolidone (PVP) were admixed and the mixture was fed through the hopper to the main feeding port of a twin-screw extruder equipped with the same screws as described in Example 1 and a 0.7 mmφ×8-orifice die at a rate of 20 g/min. The operating temperature was set at 100° C. for the respective barrels and die, and with 30% (w/w) triethyl citrate being added through the auxiliary feeding port at a rate of 2 ml/min., the load was processed and extruded at a screw rotational speed of 100 rpm to provide an swollen molding of the invention.

EXAMPLE 11

Fifty (50) grams of diclofenac sodium, 100 g of hydroxypropylmethylcellulose acetate succinate, 60 g of sodium hydrogen carbonate, and 90 g of low substituted hydroxypropylcellulose were admixed and the mixture was fed through the hopper to the main feeding port of a twin-screw extruder equipped with the same screws as described in Example 1 and a 2 mmφ×1-orifice die at a rate of 30 g/min. The operating temperature was set at 120° C. for the respective barrels and die and with purified water being added through the auxiliary feeding port at a rate of 2 ml/min., the load was processed and extruded at a screw rotational speed of 100 rpm to provide an swollen molding of the invention.

EXAMPLE 12

Fifty (50) grams of diphenidol hydrochloride, 70 g of hydroxypropylmethylcellulose acetate succinate, 20 g of sodium hydrogen carbonate, and 60 g of low substituted hydroxypropylcellulose were admixed and the mixture was fed through the hopper to the main feeding port of a twin-screw extruder equipped with the same screws and die as described in Example 1 at a rate of 30 g/min. The operating temperature was set at 120° C. for the respective barrels and die and with purified water being added through the auxiliary feeding port at a rate of 2 ml/min., the load was processed and extruded at a screw rotational speed of 100 rpm to provide an swollen molding of the invention.

Comparison Example 1

Twenty (20) grams of nicardipine hydrochloride and 230 g of hydroxypropylmethylcellulose acetate succinate were admixed and the mixture was fed through the hopper to the main feeding port of a twin-screw extruder equipped with the same screws and die as used in Example 1 at a rate of 30 g/min. The operating temperature was set at 120° C. for the respective barrels and die and with purified water being added through the auxiliary feeding port at a rate of 2 ml/min., the load was processed and extruded at a screw rotational speed of 80 rpm to provide a molding.

Comparison Example 2

Twenty (20) grams of nicardipine hydrochloride, 220 g of hydroxypropylmethylcellulose acetate succinate, and 10 g of dried aluminum hydroxide gel (4% (w/w)) were admixed and the mixture was processed and extruded under the same conditions as used in Comparison Example 1 to provide a molding.

Test Example 1

The porosity distribution of the swollen moldings obtained in Examples 1 and 2 and the moldings obtained in Comparison Examples 1 and 2 was determined by the mercury injection method (equipment: Poresizer 9320, Shimadzu). Each artifact was cut to lengths of about 8–12 mm and pretreated (dried under reduced pressure at about 50° C. for 15 hours) before determination.

[TABLE 1]

| | Porosity (%) | Pore volume (cc/g) | Mean pore diameter (μm) | Bulk density (g/cc) |
|---|---|---|---|---|
| Example 1 | 88.8 | 6.374 | 19.5 | 0.139 |
| Example 2 | 61.2 | 1.805 | 11.0 | 0.339 |
| Comparison Example 1 | 7.4 | 0.062 | 0.02 | 1.194 |
| Comparison Example 2 | 26.2 | 0.280 | 13.2 | 0.935 |

[Porosity: the percentage of the pore volume of a sample relative to the volume of the sample including the pores and intergranular spaces.
Pore volume: the integral mercury-filled pore volume of a sample from initial mercury injection pressure to maximum pressure at determination divided by the weight of the sample.
Mean pore diameter (the median value of pore diameter): the pore diameter value corresponding to the median value between the minimum and maximum pore volumes in the integral porosity distribution.
Bulk density: the density value calculated from the weight of a sample and the volume of the sample at the mercury injection pressure]

It is apparent from Table 1 that whereas the swollen moldings obtained in Examples 1 and 2 had large values of porosity and pore volume, which represent the availability of internal space, the moldings obtained in Comparison Examples 1 and 2 which were either devoid of an auxiliary blowing agent or lean in the agent showed only small corresponding parameter values, indicating that the latter moldings contained small internal spaces. Moreover, the swollen moldings of Examples 1 and 2 showed very low bulk density values.

Thus, the swollen molding of the invention has a large internal void volume and, moreover, its mean pore diameter is as small as 10–20 μm.

Test Example 2

The swollen moldings obtained in Examples 1 and 2 and the moldings obtained in Comparison Examples 1 and 2 were determined for strength against shaking and floatability at various points of time.

A 200 ml separatory funnel was charged with 100 ml of JP (Japanese Pharmacopoeia) No. 1 Fluid and each sample was placed in the fluid and shaken on a KH Shaker (Model V. S, amplitude 5 cm, shaking frequency 300/min., Iwaki) for 6 hours. Sampling was serially made for floatability and morphological evaluations.

Evaluation of floatability was performed using a micro-load transducer (UL-10GR, Shinkoh-Minevea). Thus, the sample was set to the transducer via a fixing attachment and the force required to submerge the sample in JP No. 1 Fluid was electrically measured.

Each sample consisted in a 2 cm-long strip. As a control floating capsule, Barrelieze (registered trade mark, No. 2 size) containing diazepam as an active ingredient and available commercially in West Germany was simultaneously tested.

It is apparent from FIG. 1 that the swollen moldings obtained in Examples 1 and 2 floated immediately after placement in the test fluid and although their floatability was somewhat sacrificed by shaking, they continued to float even after 4 hours in the case of Example 1 and 6 hours in the case of Example 2.

On the other hand, the moldings obtained in Comparison Examples 1 and 2 sank either immediately after placement in the test fluid or soon after the beginning of shaking. These floating behaviors endorsed the results of Test Example 1.

In addition, whereas the control capsule was completely disintegrated by 1 hour of shaking, the samples of Examples 1 and 2 had not been disintegrated even after 4 hours and 6 hours, respectively, indicating the high strength of these swollen moldings. Test Example 3.

According to JP Dissolution Test, Method 2 (paddle method), the swollen molding of the invention was subjected to a release test using 900 ml of No. 1 Fluid and a paddle speed of 100 rpm.

For use in this release test, each swollen molding of the invention was crushed using a roll granulator (GRN-1041, Japan Granulator) into granules within the range of Sieve No. 16 (1000μ) to Sieve No. 30 (500μ).

1) From granules of the swollen moldings obtained in Examples 1, 2 and 3, the amount equivalent to 20 mg of nicardipine hydrochloride was respectively weighed and subjected to a release test. Sampling was made serially and the nicardipine hydrochloride concentration of each sample was determined by high performance liquid chromatography.

Figure 2:
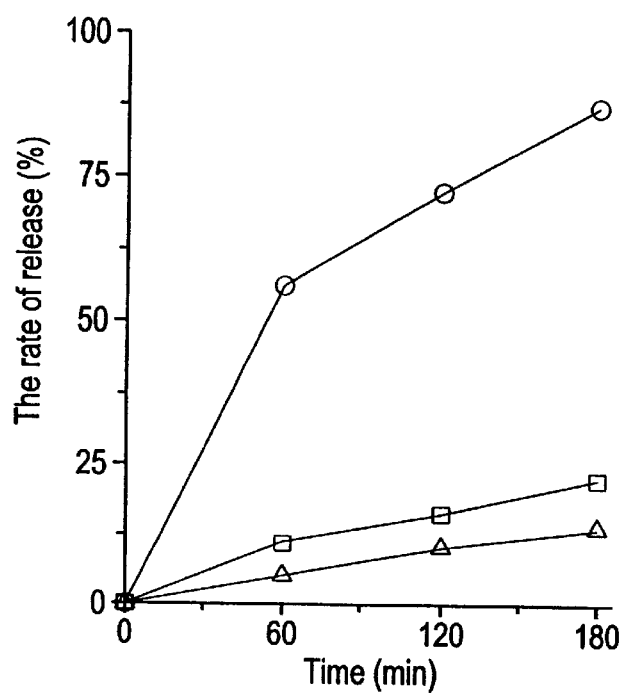
FIGS. 2–5 are graphs of various time release tests.

A shown in FIG. 2, the swollen moldings of the invention showed mild release patterns while they were afloat, indicating that a desired release pattern can be obtained by varying the addition level of the drug release control agent.

2) From granules of the swollen moldings obtained in Examples 7 and 8, the amount equivalent to 10 mg of oxybutynin hydrochloride was respectively weighed and subjected to a release test. Sampling was performed serially and the oxybutynin hydrochloride concentration of each sample was determined by high performance liquid chromatography.

Figure 3:
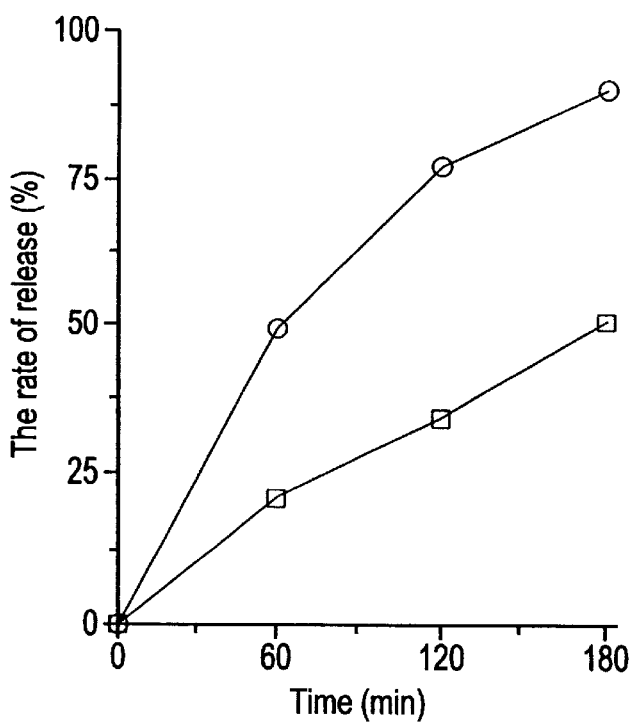

The results indicated that the swollen moldings of the invention showed mild release patterns while they were afloat as depicted in FIG. 3 and that a desired release pattern can be obtained by varying the addition level of the drug release control agent.

3) From granules of the swollen molding obtained in Example 11, the amount equivalent to 25 mg of diclofenac sodium was weighed and subjected to a release test. Sampling was performed serially and the diclofenac sodium concentration of each sample was determined by high performance liquid chromatography.

Figure 4:
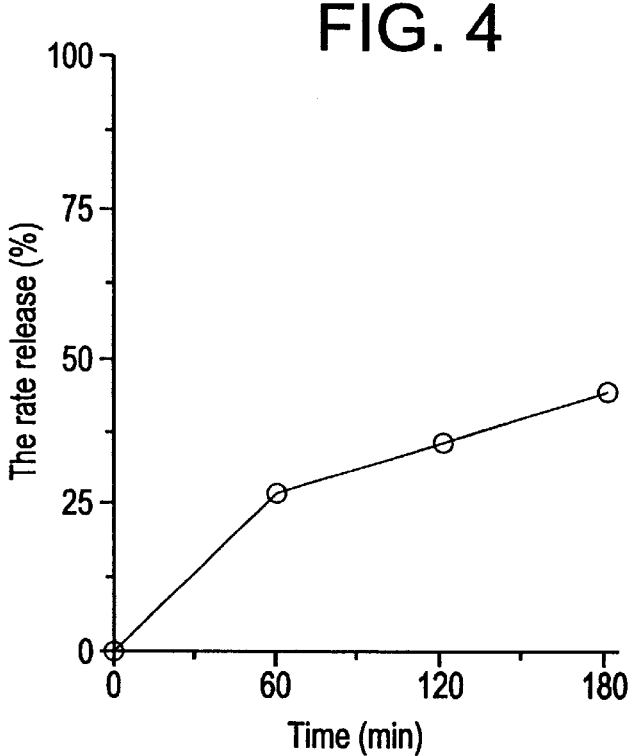

The swollen molding of the invention showed a mild release pattern while its was afloat as depicted in FIG. 4.

4) From granules of the swollen molding obtained in Example 12, the amount equivalent to 25 mg of diphenidol hydrochloride was weighed and subjected to a release test. Sampling was performed serially and the diphenidol hydrochloride concentration of each sample was determined by high performance liquid chromatography.

Figure 5:
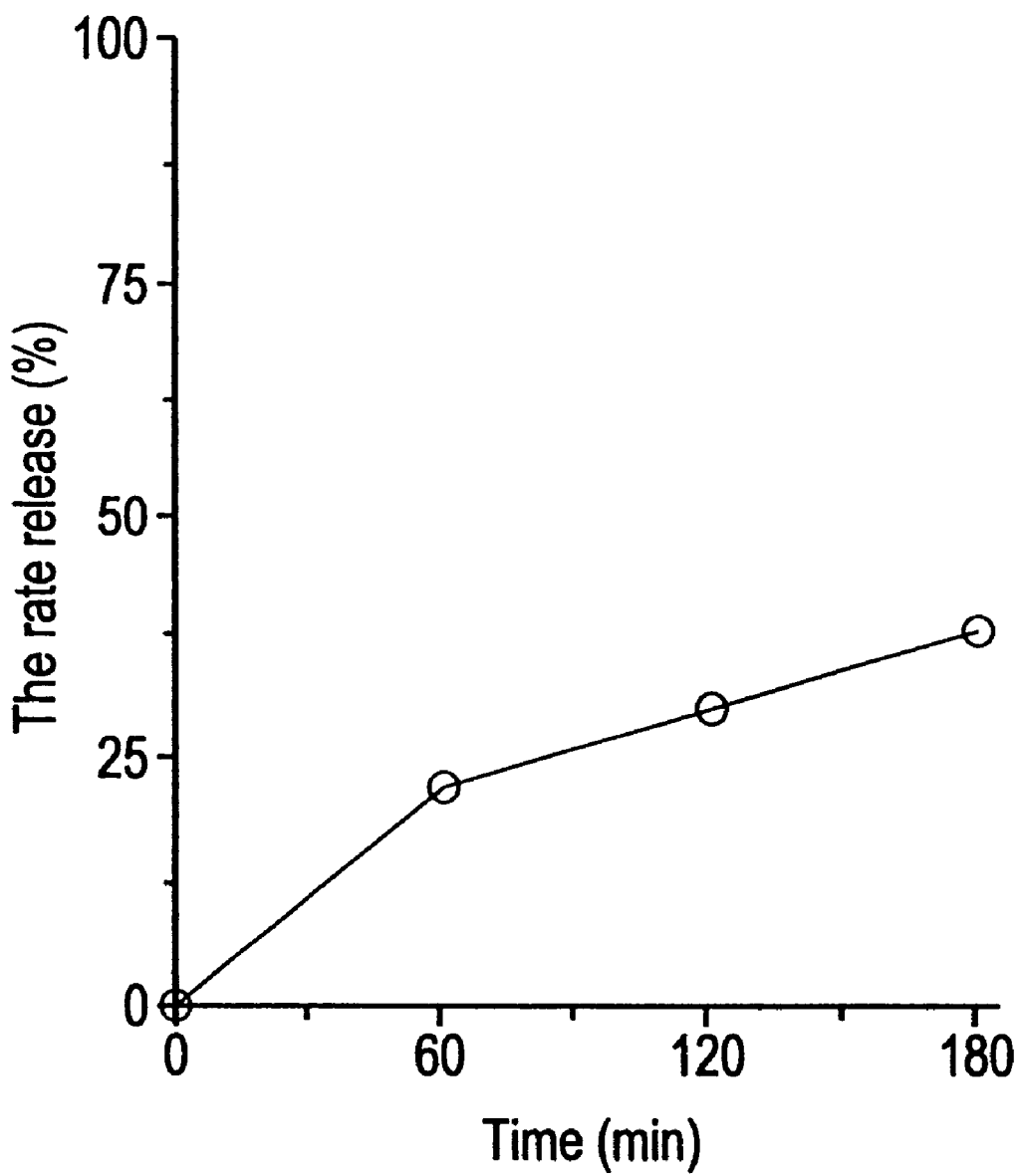

The swollen molding of the invention showed a mild release pattern while its was afloat as depicted in FIG. 5.

BRIEF DESCRIPTION OF THE DRAWINGS

The results of floatability evaluation are shown in FIG. 1, where the abscissa represents time (in hours) and the ordinate represents floatability (mg). —o— represents the floatability of the swollen molding of the invention as obtained in Example 1; —□— represents the floatability of the swollen molding obtained in Example 2; —Δ— represents the floatability of the molding obtained in Comparison Example 1; —∇— represents the floatability of the molding obtained in Comparison Example 2, and —●— represents the floatability of the control capsule.

The results of a release test are shown in FIG. 2, where the abscissa represents release time (in minutes) and the ordinate represents the rate of release (%) of nicardipine hydrochloride. —o— represents the release curve of the swollen molding of the invention as obtained in Example 1; —□— represents the release curve of the swollen molding of the invention as obtained in Example 2; and —Δ— represents the release curve of the swollen molding of the invention as obtained in Example 3.

The results of another release test are shown in FIG. 3, where the abscissa represents release time (in minutes) and the ordinate represents the rate of release (%) of oxybutynin hydrochloride. —o— represents the release curve of the swollen molding obtained in Example 7 and —□— represents the release curve of the swollen molding obtained in Example 8.

The results of another release test are shown in FIG. 4, where the abscissa represents release time (in minutes) and the ordinate represents the rate of release (%) of diclofenac sodium. —o— represents the release curve of the swollen molding obtained in Example 11.

The results of still another release test are shown in FIG. 5, where the abscissa represents release time (in minutes) and the ordinate represents the rate of release (%) of diphenidol hydrochloride. —o— represents the release curve of the swollen molding obtained in Example 12.

What is claimed is:

1. An extruded expanded gastric molding for a sustained release preparation comprising an extruded pharmaceutically acceptable acid resistant polymer or co-polymer which is capable of being expanded into a microfine porous structure, as a predominant component comprising at least 25% by weight of the molding, and a pharmaceutical drug substance, with said polymer compound having been physically reacted with sufficient auxiliary blowing agent, during extrusion of the polymer compound and the drug substance; to provide said microfine porous structure with a mesh-like cross section in the extruded molding and an apparent density of less than 1, whereby the microfine porous molding is capable of floating on gastric fluids for sustained release of the pharmaceutical drug substance.

2. A swollen molding according to claim 1 wherein said acid-resistant polymer or co-polymer is a pH-dependent coating agent polymer or a pH-independent coating agent polymer.

3. A swollen molding according to claim 1 wherein said acid-resistant polymer is selected from the group consisting of hydroxypropylmethylcellulose acetate succinate, hydroxypropylmethyl cellulose phthalate, methacrylic copolymer, carboxymethylethylcellulose, cellulose acetate phthalate, ethylcellulose, and aminoalkyl methacrylate copolymer.

4. A swollen molding according to claim 1 wherein said acid-resistant polymer is selected from the group consisting of hydroxypropylmethylcellulose acetate succinate, hydroxypropylmethyl cellulose phthalate, methacrylic copolymer, carboxymethylethylcellulose, cellulose acetate phthalate, ethylcellulose, and aminoalkyl methacrylate copolymer and said auxilary blowing agent is selected from the group consisting of dried aluminum hydroxide gel, synthetic aluminosilicate, calcium hydrogen phosphate, calcium carbonate, precipitated calcium carbonate, calcium hydrogen carbonate, and talc.

5. A method of producing the swollen molding of claim 1 characterized in that all the components thereof and water are processed in a lump using a multi-screw extruder.

6. A method according to claim 5 wherein said multi-screw extruder is a twin-screw extruder.

7. A sustained release preparation comprising the swollen molding of claim 1.

8. The gastric molding of claim 1 wherein the microfine porous structure comprises a porosity of from about 61.2% to about 88.8% a mean pore diameter of from about 10 $\mu$m to about 20 $\mu$m.

* * * * *